United States Patent
Davis et al.

(10) Patent No.: US 8,664,459 B2
(45) Date of Patent: Mar. 4, 2014

(54) PROCESS FOR HYDROGENATING OLEFINS

(75) Inventors: Ruth A. Davis, Allentown, PA (US); Norman Macleod, Hartlepool (GB); Gordon Edward Wilson, Stockton-on-Tees (GB)

(73) Assignees: Air Products and Chemicals, Inc., Allentown, PA (US); Johnson Matthey PLC, London (GB)

( * ) Notice: Subject to any disclaimer, the term of this patent is extended or adjusted under 35 U.S.C. 154(b) by 1094 days.

(21) Appl. No.: 12/264,443

(22) Filed: Nov. 4, 2008

(65) Prior Publication Data
US 2009/0247800 A1   Oct. 1, 2009

Related U.S. Application Data

(60) Provisional application No. 61/040,912, filed on Mar. 31, 2008.

(51) Int. Cl.
*C07C 5/02* (2006.01)

(52) U.S. Cl.
USPC ........... 585/275; 585/250; 585/276; 585/258; 585/259; 585/260; 585/261; 585/262; 585/263

(58) Field of Classification Search
USPC ................. 585/275, 276, 258, 259, 260–263; 423/230, 231, 210, 244.1, 244.09; 208/89
See application file for complete search history.

(56) References Cited

U.S. PATENT DOCUMENTS

| | | | | |
|---|---|---|---|---|
| 3,689,401 A | * | 9/1972 | Gomi et al. | 208/57 |
| 4,371,507 A | * | 2/1983 | Farha et al. | 423/230 |
| 7,037,485 B1 | | 5/2006 | Drnevich et al. | |
| 2004/0260131 A1 | | 12/2004 | Bergmeister et al. | |

(Continued)

FOREIGN PATENT DOCUMENTS

| CN | 1200397 | 12/1998 |
|---|---|---|
| CN | 1200397 A | 12/1998 |

(Continued)

OTHER PUBLICATIONS

Hao, Shu-ren, "Hydrocarbon Steam-Reforming Process: Feedstock and Catalysts for Hydrogen Production in China" Int. J. Hydrogen Energy, vol. 23, No. 5,pp. 315-319, May 1, 1998.

(Continued)

*Primary Examiner* — In Suk Bullock
*Assistant Examiner* — Sharon Pregler
(74) *Attorney, Agent, or Firm* — Stradley Ronon Stevens & Young, LLP (57) ABSTRACT

A process for hydrogenating olefins is disclosed. The olefins are present in a feed gas which includes $H_2$ and one or more sulfur compounds. The sulfur compounds may include $H_2S$ and organic sulfur compounds. The feed gas is passed through a reactor at an inlet temperature from 100° C. to 250° C. The reactor contains a catalyst which is active at the inlet temperature. The reactor may be adiabatic. Saturated hydrocarbons are formed from the olefins. A temperature gradient may be formed in the reactor due to the exothermic nature of the hydrogenation reaction, causing the temperature to increase downstream in the reactor. At temperatures higher than the inlet temperature, $H_2S$ may be formed from organic sulfur compounds. A gas mixture including saturated hydrocarbons, $H_2S$ and $H_2$ exits the reactor and may be brought into contact with a chemical adsorbent which removes the $H_2S$. The gas stream may then be passed to a steam methane reformer.

27 Claims, 3 Drawing Sheets

(56) References Cited

U.S. PATENT DOCUMENTS

| | | | |
|---|---|---|---|
| 2005/0137434 A1* | 6/2005 | Li et al. | 585/258 |
| 2006/0173224 A1* | 8/2006 | Putman et al. | 585/258 |
| 2008/0237090 A1* | 10/2008 | Musich et al. | 208/89 |
| 2008/0253949 A1 | 10/2008 | Ripperger | |

FOREIGN PATENT DOCUMENTS

| | | |
|---|---|---|
| CN | 1272398 A | 11/2000 |
| CN | 1069915 C | 8/2001 |
| CN | 1351127 A | 5/2002 |
| CN | 1094072 C | 11/2002 |
| CN | 1415532 A | 5/2003 |
| CN | 1163574 C | 8/2004 |
| CN | 1184136 C | 1/2005 |
| CN | 1809521 A | 7/2006 |
| CN | 101113126 A | 1/2008 |
| EP | 0 989 093 A2 | 3/2000 |
| EP | 0 989 093 A3 | 3/2000 |
| GB | 1588763 | 4/1981 |
| GB | 2183670 A | 6/1987 |
| WO | WO 2006/056594 A1 | 6/2006 |

OTHER PUBLICATIONS

Carnell, P.J.H. and Denny, P.J., "New Feedstock Purification System Reduces Operating Costs and Allows Faster Start-Up," Ammonia Plant Safety and Related Facilities 1987, pp. 99-105, vol. 27.

Wang, Shaohu, Shen, Binglong, and Qu, Lianglong, "Commercial Application of Titania-Supported Hydrodesulfurization Catalysts in the Production of Hydrogen Using Full-Range FCC Off-Gas," Catalysis Today, 2004, pp. 339-342, vol. 98.

* cited by examiner

PROCESS FOR HYDROGENATING OLEFINS

CROSS-REFERENCE TO RELATED APPLICATION

This application claims the benefit of priority to U.S. Provisional Patent Application Ser. No. 61/040,912, filed on Mar. 31, 2008, the contents of which are incorporated herein by reference in its entirety.

FIELD OF THE INVENTION

This invention concerns a process for hydrogenating olefins.

BACKGROUND OF THE INVENTION

Refinery off gases can provide a source of hydrogen which can be used by others or used in the refinery itself. The off gases comprise $H_2$ as well as hydrocarbons which can be converted to $H_2$. The off gases from various different processes in the refinery may be combined to form a refinery fuel gas feed (RFG feed). The RFG feed can be used as feed for a steam methane reformer to produce $H_2$ required, for example, for refinery hydrocracking and desulfurization units.

While the RFG feed is potentially a rich source of hydrogen, its utilization is not without problems. The RFG feed, being a mixture of off gases from a number of different processes, comprises a wide variety of constituents, some of which are detrimental to the steam methane reforming process. Such constituents include olefins such as ethylene, propylene, butenes and other alkenes as well as sulfur compounds such as mercaptans, sulfides, COS and thiophenes. Particular examples of these sulfur compounds include $H_2S$, COS, methyl mercaptan, ethyl mercaptan, dimethyl sulfide and thiophene. Before such a gas mixture can be processed in a steam methane reformer, the various olefins must be hydrogenated to avoid coking of the steam methane reformer catalyst, and the sulfur compounds must be removed to avoid catalyst poisoning.

Another difficulty in the utilization of RFG feed arises because both the composition and available volume of the feed may vary substantially over relatively short time periods. For example, the concentration of olefins and hydrogen in an RFG feed may vary significantly during daily operation.

Prior art methods for pre-treating RFG feeds to steam methane reforming involve hydrogenating the olefins by reacting the RFG feed with hydrogen in an adiabatic reactor containing a catalyst comprising a support, such as alumina, impregnated with metal compounds, such as Co, Mo, and Ni types of hydrogenation catalysts. Organic sulfur compounds are also hydrogenated in the presence of these catalysts to produce $H_2S$, which may then be removed by passing the processed feed through a bed of zinc oxide. The resultant gas stream may then be processed in a steam methane reactor.

One disadvantage of known prior art processes is that they cannot readily handle concentrations of olefins greater than 4 to 6 mole %, and cannot adapt to the full potential variability of the feed gas composition. This is due to the highly exothermic nature of the olefin hydrogenation reaction combined with the relatively high reactor inlet temperatures necessary to initiate hydrogenation in the presence of the catalysts. Temperatures in the hydrogenation reactor are limited to a maximum of 398-427° C. to prevent hydrocarbon cracking, which is undesirable. With typical inlet temperatures from 249° C. to 302° C. (depending upon the choice of catalyst), the maximum temperature limit of 398-427° C. imposes a limit on the olefin concentration from 4 to 6 mole % for an adiabatic reactor.

Prior art methods which address this problem of high olefin concentration include blending natural gas with the RFG feed as necessary in order to dilute the olefin concentration to an acceptable level, or recycling some of the outlet gas from the reactor to dilute the RFG feed. The use of an isothermal reactor upstream of an adiabatic reactor in series has also been considered. These solutions tend to restrict RFG utilization, or they are expensive, consume more power and require more complicated equipment and controls as well as larger capacity equipment. There is clearly a need for a hydrogenation process that can handle concentrations of olefins in an adiabatic reactor higher than 4 to 6% without exceeding the maximum temperature limitations.

SUMMARY OF THE INVENTION

The invention concerns a process for hydrogenating olefins. The process comprises:
  (a) introducing a feed gas comprising an olefin, $H_2$, and at least one sulfur compound through an inlet of a reactor vessel at an inlet temperature from 100° C. to 250° C., the reactor vessel containing a sulfided metal catalyst on a support, the catalyst comprising from 2 wt % to 20 wt % NiO and from 9 wt % to 40 wt % $MoO_3$ on an unsulfided basis;
  (b) contacting the olefin and the $H_2$ with the catalyst to react the olefin and the $H_2$ under reaction conditions effective to produce a saturated hydrocarbon; and
  (c) withdrawing an outlet gas mixture comprising the saturated hydrocarbon from the reactor vessel through an outlet at an outlet temperature from 120° C. to 425° C.

The sulfur compound may comprise an organic sulfur compound. The process may further comprise, before withdrawing the outlet gas mixture, contacting the organic sulfur compound and the $H_2$ with the catalyst at a temperature from 120° C. to 425° C. thereby forming $H_2S$ from the organic sulfur compound. The organic sulfur compound may be selected from the group consisting of carbonyl sulfide, carbon disulfide, mercaptans, dialkyl sulfides, dialkyl disulfides, thiophenic species and combinations thereof. The outlet gas mixture comprises $H_2S$.

The process may further comprise:
  (d) introducing the outlet gas mixture into a second reactor containing a chemical adsorbent comprising ZnO;
  (e) contacting the outlet gas mixture with the chemical adsorbent at a temperature from 200° C. to 425° C. to remove sulfur therefrom and produce a sulfur depleted outlet gas; and
  (f) withdrawing the sulfur depleted outlet gas from the second reactor.

The process may further comprise contacting the organic sulfur compound and $H_2$ with a different catalyst selected from the group consisting of cobalt-molybdenum, nickel molybdenum, cobalt-tungsten, nickel tungsten, nickel-cobalt-molybdenum based catalysts and combinations thereof at a temperature from 200° C. to 425° C., thereby forming $H_2S$ from the organic sulfur compound.

The invention also encompasses a process for preparing a feed gas for steam methane reforming. The feed gas comprises at least one olefin, $H_2$ and at least one sulfur compound. The process comprises:
  (a) reacting the olefins with the $H_2$ in the presence of a sulfided catalyst comprising from 2 wt % to 20 wt % NiO and 9 wt % to 40 wt % $MoO_3$ on an unsulfided basis at an initial temperature from 100° C. to 250° C., thereby producing an outlet gas mixture comprising saturated hydrocarbons;
(b) where the sulfur compound comprises at least one organic sulfur compound, the process includes further contacting the outlet gas mixture with the catalyst at a temperature from 120° C. to 425° C. thereby forming $H_2S$ from the sulfur compounds;
(c) removing the outlet gas mixture from the presence of the catalyst at a temperature from 120° C. to 425° C.; and
(d) contacting the outlet gas mixture with a chemical adsorbent comprising ZnO at a temperature from 200° C. to 425° C. to remove sulfur therefrom.

DETAILED DESCRIPTION OF EMBODIMENTS

Figure 1:
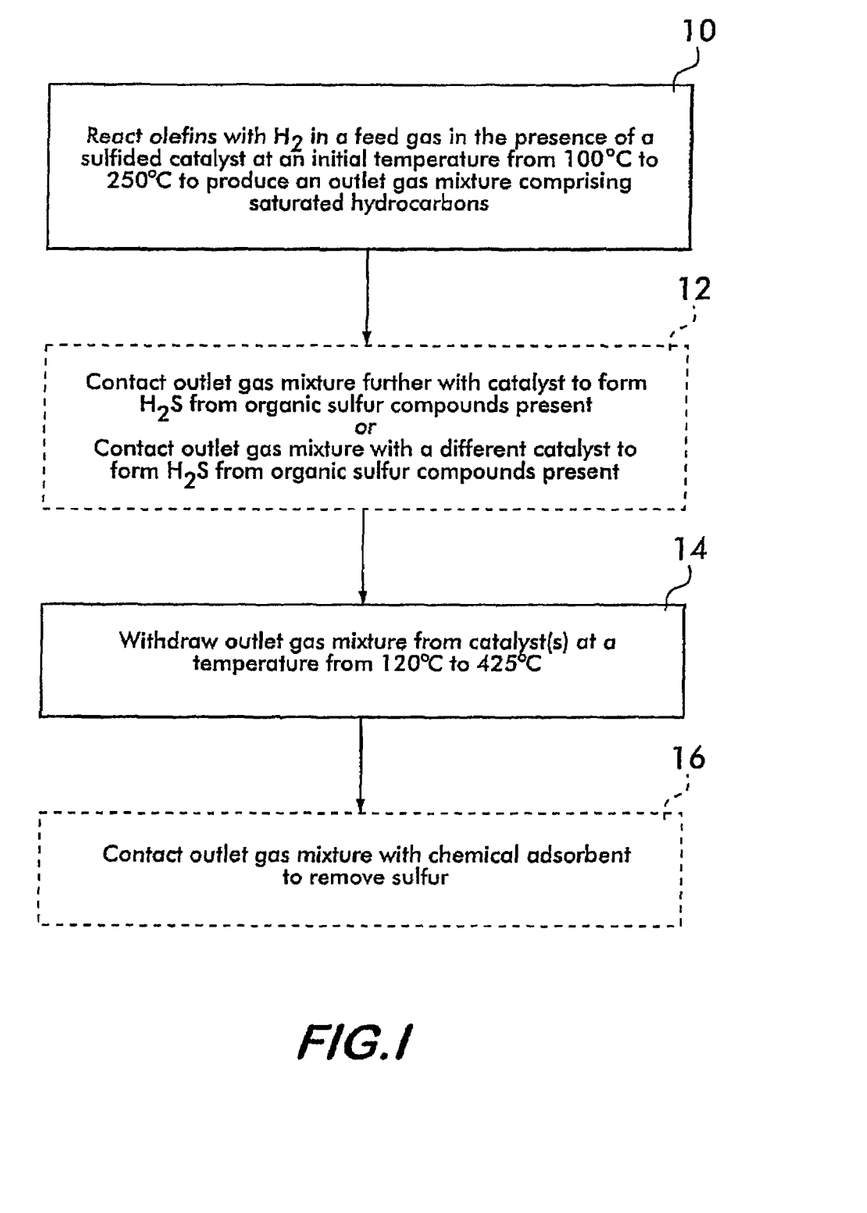
FIG. 1 is a flow chart illustrating a process according to the invention.

FIG. 1 shows a flow chart illustrating a process for hydrogenating olefins according to the invention. As used herein the term "olefin" refers to an aliphatic hydrocarbon having at least one point of unsaturation, i.e., a double bond. Examples of olefins include ethylene, propylene, butenes and pentenes. The olefins are present in a feed gas, for example, a refinery fuel gas stream comprising a mixture of off gases from various different refinery processes. The feed gas also includes $H_2$ and a sulfur compound. Sulfur compounds include, for example, carbonyl sulfide, carbon disulfide, mercaptans such as methyl mercaptan, dialkyl sulfides such as dimethyl sulfide, dialkyl disulfides such as diethyl disulfide, thiophenic species and $H_2S$.

In the process, as shown at 10, the olefins are reacted with the $H_2$ in the presence of a sulfided metal oxide catalyst. A sulfided catalyst is a catalyst which has been exposed to sulfur, or a sulfur compound wherein at least a portion of the metal oxide present in the catalyst is converted to active metal sulfides. The catalyst may be obtained pre-sulfided or it may be obtained unsulfided and sulfided in situ, for example, in the reactor vessel in which the process will be carried out. The catalyst used in the process according to the invention comprises from 2 wt % to 20 wt % NiO and from 9 wt % to 40 wt % $MoO_3$ on an unsulfided basis, i.e., in the unsulfided state. The wt % on an unsulfided basis is the wt % not accounting for sulfur in the weight calculation. In one embodiment, the catalyst may comprise from 3 to 4 wt % NiO, 5 to 6 wt % NiO, or about 3.5 wt % NiO on an unsulfided basis. The catalyst may also comprise 9 to 11 wt % $MoO_3$, 24 to 26 wt % $MoO_3$, or about 10.5 wt % $MoO_3$. The olefins and $H_2$ are initially reacted in the presence of the catalyst at a temperature from 100° C. to 250° C. In one embodiment, the initial temperature may be from 100° C. to 175° C. In another embodiment, the initial temperature may be from 100° C. to 225° C. The initial temperature is the temperature at which the olefins and $H_2$ are first brought into the presence of the catalyst. In a practical example, described in detail below, the initial temperature is the inlet temperature to a reactor. The olefins and $H_2$ react in the presence of the catalyst to produce an outlet gas mixture comprising saturated hydrocarbons.

If the feed gas contains organic sulfur compounds such as mercaptans, sulfides, COS and thiophenes and is being pre-treated for use as a feed to a steam methane reformer, the process further comprises reacting the outlet gas mixture with the catalyst at a temperature from 120° C. to 425° C. to form H2S from the sulfur compounds as shown at 12. The catalyst may, therefore, serve as a catalyst for the hydrogenation of olefins and sulfur. Alternately, the outlet gas mixture may be reacted with a different catalyst, for example, a different Ni/Mo or a Co/Mo catalyst at a temperature from 200° C. to 425° C. to form $H_2S$ from the sulfur compounds.

As shown at 14, the outlet gas mixture is withdrawn from the catalyst at a temperature from 120° C. to 425° C. The temperature of the outlet gas mixture is higher because the hydrogenation reaction is exothermic, and the process is preferably run substantially adiabatically. In this process, the terms "adiabatic" and "adiabatically" mean that there is no forced convection heat transfer. Heat may be introduced by conduction, radiation and/or natural convection. In forced convection, motion of a cooling or heating fluid is the result of an outside force, as might be exerted by a pump impeller. The upper temperature limit is defined to prevent hydrocarbon cracking. Hydrocarbon cracking is the breakdown of hydrocarbons, e.g., into elemental carbon, which can damage or reduce the effectiveness of the catalyst.

As shown at 16, the sulfur is removed by contacting the outlet gas mixture with a chemical adsorbent comprising ZnO at a temperature from 200° C. to 400° C.

Figure 2:
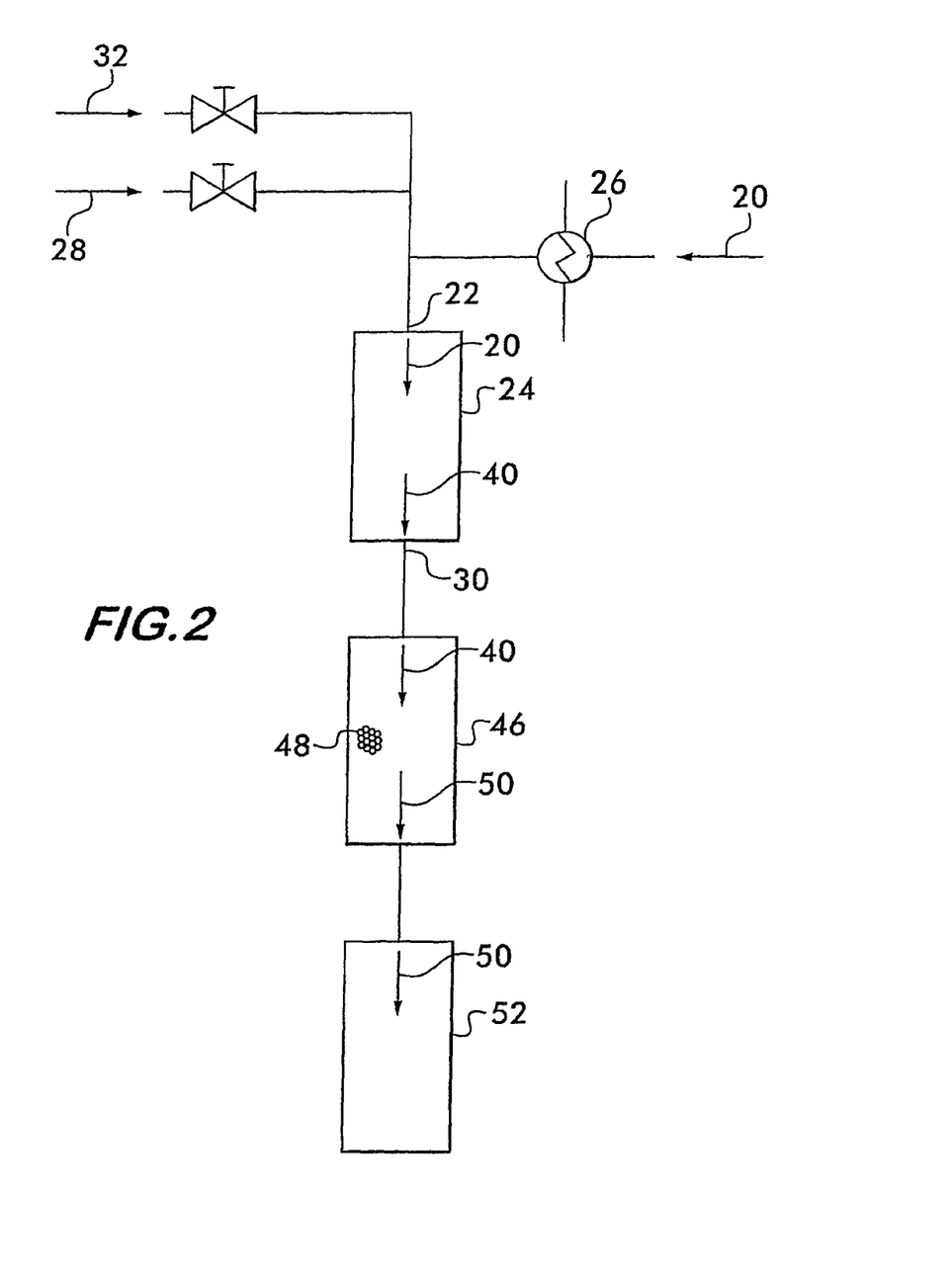
FIG. 2 is a schematic diagram illustrating a practical application of the process according to the invention.

FIG. 2 illustrates a hydrogenation reactor process scheme according to the invention. A feed gas 20, for example, a refinery fuel gas comprising a mixture of one or more olefins, $H_2$, and at least one sulfur compound, and which may also comprise $O_2$, is supplied to the inlet 22 of a reactor 24. For the hydrogenation process according to the invention it is advantageous that the feed gas temperature at the inlet be as low as possible while still ensuring catalyst activity. A relatively low inlet temperature, for example, from 100° C. to 250° C., allows feed gas having an olefin concentration greater than 4 to 6 mole % to be processed using the catalysts as specified without the reactor temperature exceeding the value at which hydrocarbon cracking will begin. The temperature within the reactor 24 will tend to rise because the hydrogenation reactions of the olefins are exothermic and the reactor is run substantially adiabatically, i.e., the reactor is not actively cooled or heated (although there will be some heat loss to the ambient due to conduction, radiation and/or natural convection). An adiabatic process is advantageous because it simplifies the apparatus and the control systems, reducing capital costs for the equipment. It is also possible to run the process substantially isothermally by actively cooling the reactor, for example, using a shell/tube reactor with a coolant. Cooling may be provided to maintain the reactor within a desired temperature range. To ensure that the desired feed gas temperature at the reactor inlet 22 is maintained, a heat exchanger 26 is provided upstream of the reactor 24 to heat or cool the feed gas 20 as needed.

As the composition of the feed gas is expected to vary widely, provision is preferably also made for the addition of $H_2$ to the feed gas upstream of the reactor from a separate $H_2$ source 28. Sufficient $H_2$ is provided to the reactor to prevent hydrocarbon cracking, and it has been found that if sufficient $H_2$ is provided at the inlet 22 so that there is at least 2 mole % $H_2$ at the outlet 30 of the reactor 24, then hydrocarbon cracking will not occur. One skilled in the art is capable of determining the inlet concentration of $H_2$ needed to provide at least 2 mole % $H_2$ at the outlet. The desired $H_2$ concentration may be present either in the feed gas 20 as received or by the addition of $H_2$ from the source 28 if necessary. Provision may also be made for the addition of a gaseous hydrocarbon upstream of the reactor from a separate source 32. The source 32 may provide, for example, natural gas, which is supplied to keep the process running at those times when insufficient feed gas is available. This simplifies shutdowns and startups of the process and also provides the option of diluting the feed gas 20 if the concentration of olefins therein exceeds the amount which the process can handle without exceeding the upper temperature limits in the reactor.

Figure 3:
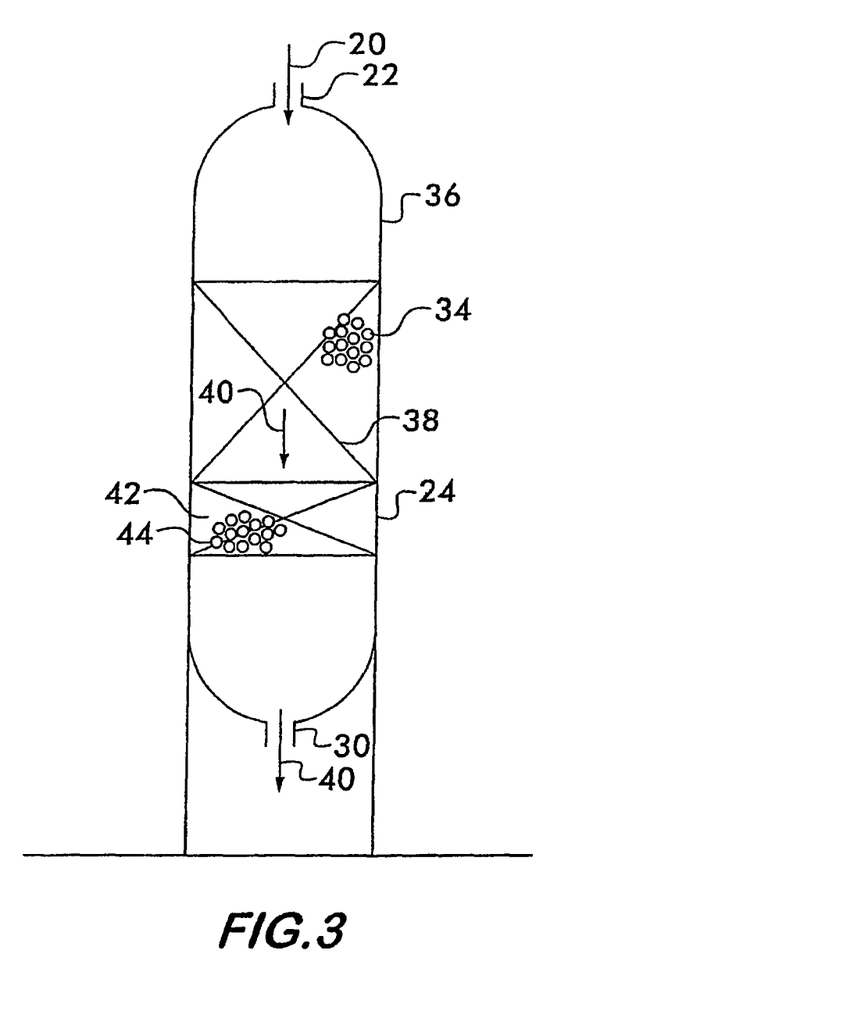
FIG. 3 is a schematic diagram illustrating a reactor vessel shown in FIG. 2.

As illustrated in FIG. 3, feed gas 20 enters the reactor 24 at an initial or inlet temperature from 100° C. to 250° C. and the olefins present in the feed gas react with the $H_2$ in the presence of a catalyst 34 to produce saturated hydrocarbons. Catalyst 34 comprises a support, for example, an alumina, titania or zirconia, which is permeated with a sulfided metallic composition. In a preferred process according to the invention, an alumina support is impregnated with a metallic composition, dried and calcined such that a metal oxide catalyst is formed comprising (in the unsulfided state) between 2 wt % to 20 wt % NiO and 9 wt % to 40 wt % $MoO_3$. In a particular embodiment, the catalyst (unsulfided) may comprise 3.5 wt % NiO and 10.5 wt % $MoO_3$, with the balance being the alumina support. A catalyst having this composition is sold by Johnson Matthey under the tradename KATALCO 61-1T. A pre-sulfided catalyst is also available from Johnson Matthey under the tradename KATALCO 61-1TS. In another embodiment, the catalyst (unsulfided) may comprise 5.2 wt % NiO and 26 wt % $MoO_3$ with the balance being the alumina support. A catalyst having this composition is sold by Johnson Matthey under the tradename KATALCO 61-2T. A pre-sulfided catalyst is also available from Johnson Matthey under the tradename KATALCO 61-2TS.

In use, the catalyst 34 must remain sulfided, and for proper operation therefore, it is preferred that the feed gas comprise one or more sulfur compounds, preferably $H_2S$ at an $H_2S$ concentration of at least 2 volume ppm to avoid sulfur from being stripped from the catalyst. As noted, other sulfur species may also be present in concentrations that prevent sulfur stripping of the catalyst.

The catalyst may be provided as shaped units designed to maximize surface area and minimize pressure drop through the reactor. Examples of shaped units include pellets, granules, agglomerates and extrudates. They may have aspect ratios (ratios of largest to smallest dimension) from 1:1 to 3:1. Structural supports are also feasible.

As shown in FIG. 3, the reactor 24 comprises a reactor vessel 36, which holds the catalyst 34 in a catalyst bed 38. As the feed gas moves through the bed 38, the olefins are hydrogenated and an outlet gas mixture 40 is formed which comprises saturated hydrocarbons, $H_2$, $H_2S$ and other sulfur compounds originally present in the feed gas. A temperature gradient develops throughout the catalyst bed 38 with the temperature increasing between the reactor inlet 22 and the outlet 30 due to the exothermic nature of the hydrogenation reaction, and the fact that the vessel is preferably operated in a substantially adiabatic manner, i.e., it is not actively cooled. At some point in the bed, a temperature is reached whereupon organic sulfur compounds, which may be present begin to react. It may be advantageous to provide a second catalyst bed 42 within the reactor vessel 36 downstream of the bed 38. The second catalyst bed 42 may comprise a different catalyst 44, selected from cobalt-molybdenum, nickel molybdenum, cobalt-tungsten, nickel tungsten, nickel-cobalt-molybdenum based catalysts and combinations thereof.

The outlet gas mixture 40, comprising saturated hydrocarbons, $H_2$ and $H_2S$, exits the reactor vessel 36 from outlet 30 at an outlet temperature from 120° C. to 425° C., preferably with an $H_2$ concentration of about 2%. These conditions of temperature and $H_2$ concentration ensure that hydrocarbon cracking does not occur in the reactor vessel. In a practical industrial application, the reactor may be operated at a pressure from 0.6 MPa to 5 MPa and a gas hourly space velocity (GHSV) from 400 $hr^{-1}$ to 6000 $hr^{-1}$. Gas hourly space velocity is defined as the feed normal volumetric flow rate ($Nm^3/hr$) divided by the reactor vessel volume ($m^3$) which contains the catalyst, where normal conditions are based on a temperature of 0° C. and a pressure of 1 atm absolute. The reactor vessel volume which contains the catalyst is the empty volume in the reactor vessel. For example, if the reactor vessel is a cylinder with an inner diameter of 0.5 m and the catalyst bed height is 1 m, the reactor vessel volume which contains the catalyst is $$\frac{\pi \times 0.5^2}{4} \times 1 = 0.2 \text{ m}^3.$$

With reference again to FIG. 2, after exiting the reactor 24, the outlet gas mixture 40, comprising saturated hydrocarbons, $H_2$ and $H_2S$ may be conducted to a desulfurization reactor 46. The desulfurization reactor 46 holds a bed of a chemical adsorbent 48, such as ZnO. The outlet gas mixture is contacted with the adsorbent at a temperature from 200° C. to 425° C. to remove the $H_2S$ from the outlet gas mixture 40 and form a sulfur depleted feed stream 50 comprising saturated hydrocarbons and $H_2$. The feed stream 50 may be supplied to a steam methane reformer 52.

The process for hydrogenating olefins according to the invention may handle feed gases having up to 14 mole % olefins (in the absence of more than trace amounts of oxygen), and can be modified to handle olefin concentrations as great as 30 mole %. Increased olefin concentration can be achieved by, for example, operating the reactor isothermally as well as by diluting the feed gas by recycling the outlet gas mixture.

The following examples are provided which illustrate the process for hydrogenating olefins according to the invention.

EXAMPLE 1

Adiabatic Reactor

Example 1 is based upon an adiabatic reactor vessel containing a fixed-bed of catalyst. Feed gas is preheated to an inlet temperature required to initiate olefins hydrogenation, dependent on the catalyst employed. The vessel was vertically oriented with the feed gas inlet at the top and the product withdrawn from the bottom. Complete conversion of olefins to saturated hydrocarbons is achieved in the reactor product. Since the reactor is adiabatic, substantially all the heat generated by the reactions result in increasing the gas stream temperature.

The feed gas contained the following constituents:

| | |
|---|---|
| Hydrogen | 20% |
| Methane | 50% |
| C2 (Ethane + Ethylene) | 15% |
| C3 (Propane + Propylene) | 7% |
| C4 (Butane + Butene) | 2% |
| Pentane+ | 1% |
| Nitrogen | 5% |

-continued

| Olefins Breakdown: | |
|---|---|
| Ethylene | 62.5% |
| Propylene | 29% |
| Butene | 8.5% |

100 ppmv $H_2S$ + organic sulfur

Table 1 compares the olefin concentration in the feed gas achievable for the adiabatic reactor using the catalyst according to the invention, compared with the concentration attained in an adiabatic reactor using conventional catalysts, while maintaining an outlet temperature of 399° C. Data in the column designated "Prior Art" is based upon Chinese Patent Application Publication CN 1069915C.

TABLE 1

| Case | Base | Invention | Prior Art |
|---|---|---|---|
| Catalyst | Conventional | NiMo | NiCoMo/$TiO_2$ |
| Inlet T deg C. | 250 | 100 | 230 |
| Maximum Total % Olefins | 6.6 | 12.0 | 7.4 |
| Feed Composition (mole %) | | | |
| Hydrogen | 20 | 20 | 20 |
| Methane | 50 | 50 | 50 |
| Ethylene | 4.1 | 7.5 | 4.6 |
| Ethane | 10.9 | 7.5 | 10.4 |
| Propylene | 1.9 | 3.5 | 2.2 |
| Propane | 5.1 | 3.5 | 4.8 |
| Butenes | 0.6 | 1.0 | 0.6 |
| Butanes | 1.4 | 1.0 | 1.4 |
| Pentane+ | 1.0 | 1.0 | 1.0 |
| N2 | 5.0 | 5.0 | 5.0 |

The process according to the invention operates at significantly lower inlet temperatures to permit higher maximum olefin concentrations in the feed gas.

EXAMPLE 2

Catalysts KATALCO™ 61-1TS and KATALCO™ 61-2TS, available from Johnson Matthey PLC, were tested under isothermal conditions using a gas stream feed containing 15 vol % total olefins (7.5 vol % ethene, 7.5 vol % propene) and 20 vol % $H_2$. The gas stream also contained 50 volppm sulfur components (8/2/1 mix of t-butylmercaptan/thiophene/dimethyl sulfide) with balance $CH_4$. These catalysts have typical (unsulfided) compositions as shown in Table 2.

Both catalysts were tested by passing the gas stream through a bed of catalyst in a lab-scale reactor at a GHSV of 2000 $h^{-1}$ and under a pressure of 40 barg (4101 kPa (absolute)). At 120° C., under isothermal conditions, the conversion rates shown in Table 3 were achieved.

TABLE 2

| | KATALCO ™ 61-1TS | KATALCO ™ 61-2TS |
|---|---|---|
| NiO (wt %) | 3.5 | 5.2 |
| $MoO_3$ (wt %) | 10.5 | 26.0 |
| $Al_2O_3$ (wt %) | Balance | Balance |

TABLE 3

| Catalyst | vol % $C_2H_4$ Conversion | vol % $C_3H_6$ Conversion |
|---|---|---|
| KATALCO ™ 61-1TS | 44.1 | 22.8 |
| KATALCO ™ 61-2TS | 72.8 | 34.9 |

It was observed that under isothermal conditions at a temperature of 120° C., the conversion of ethylene and propylene is readily initiated. KATALCO™ 61-2TS, which has a higher nickel content, has a significantly higher catalytic activity at the desired inlet temperature than catalyst KATALCO™ 61-1TS, which has a relatively low nickel content.

Although Example 2 is based on an isothermal reactor, this example demonstrates the low temperature activity of the catalyst and provides the kinetic basis for adiabatic reactor design.

EXAMPLE 3

Example 2 was repeated using a gas stream feed containing 12 vol % total olefins (7/11/3 ratio of ethene/propene/but-1-ene) and 15 vol % $H_2$. The gas stream also contained 100 volppm sulfur components (75 volppm as 8/2/1 mix of t-butylmercaptan/thiophene/dimethyl sulfide, 25 volppm as $H_2S$) with balance $CH_4$. The catalysts were tested by passing the gas stream through a bed of catalyst in a lab-scale reactor at a GHSV of 2000 $h^{-1}$ and a pressure of 38 barg (3901 kPa (absolute)). Under isothermal conditions at ten different temperatures, the conversion rates shown in Table 4, in respect of catalyst KATALCO™ 61-1TS, and Table 5, in respect of catalyst KATALCO™ 61-2TS were achieved.

As may be clearly seen from the results, once again catalyst KATALCO™ 61-2TS, which has a higher nickel content, has a significantly higher catalytic activity than catalyst KATALCO™ 61-1TS, which has a relatively low nickel content, at the desired inlet temperatures and is a preferred catalyst for use in the process of the invention. In this case, significant olefin conversion was initiated at temperatures in the region 120-106° C.

TABLE 4

| 61-1TS | | | | |
|---|---|---|---|---|
| Temperature | | vol % $C_2H_4$ | vol % $C_3H_6$ | vol % $C_4H_8$ |
| ° C. | ° F. | Conversion | Conversion | Conversion |
| 120 | 248 | 10.6 | 3.5 | 4.8 |
| 140 | 284 | 28.7 | 9.5 | 11.5 |
| 160 | 320 | 35.9 | 13.1 | 12.4 |
| 180 | 356 | 44.4 | 17.0 | 13.9 |
| 200 | 392 | 62.2 | 27.1 | 21.1 |
| 220 | 428 | 82.0 | 47.7 | 39.2 |
| 240 | 464 | 91.6 | 62.9 | 53.6 |
| 260 | 500 | 95.7 | 71.9 | 61.6 |
| 280 | 536 | 97.2 | 82.7 | 63.8 |

TABLE 5

| 61-2TS | | | | |
|---|---|---|---|---|
| Temperature | | vol % $C_2H_4$ | vol % $C_3H_6$ | vol % $C_4H_8$ |
| ° C. | ° F. | Conversion | Conversion | Conversion |
| 120 | 248 | 25.6 | 2.8 | 8.1 |
| 140 | 284 | 72.9 | 20.2 | 18.0 |

TABLE 5-continued

| 61-2TS | | | | |
|---|---|---|---|---|
| Temperature | | vol % $C_2H_4$ | vol % $C_3H_6$ | vol % $C_4H_8$ |
| °C. | °F. | Conversion | Conversion | Conversion |
| 160 | 320 | 80.8 | 31.1 | 23.1 |
| 180 | 356 | 88.1 | 49.9 | 37.8 |
| 200 | 392 | 95.6 | 69.5 | 57.4 |
| 220 | 428 | 98.6 | 82.6 | 73.5 |
| 240 | 464 | 99.6 | 89.3 | 82.3 |
| 260 | 500 | 99.8 | 90.3 | 82.6 |
| 280 | 536 | 99.9 | 91.1 | 82.5 |

EXAMPLE 4

A gas stream feed containing 10 vol % total olefins (7/11/3 ratio of ethenelpropene/but-1-ene) and 15 vol % $H_2$ was employed. This gas stream also contained 10 volppm sulfur components (8/2/1 mix of t-butylmercaptan/thiophene/dimethyl sulfide) with balance $CH_4$. The KATALCO™ 61-2TS catalyst was in this case tested by passing the above gas stream through a bed of the catalyst in a lab-scale reactor at a GHSV of 2000 $h^{-1}$ and a pressure of 38 barg (3901 kPa (absolute)). Under isothermal conditions at ten different temperatures, the conversion rates shown in the following table with respect of catalyst KATALCO™ 61-2TS were achieved. In this case, significant olefin conversion was initiated at temperatures in the region 100-140° C.

| Temperature | | vol % $C_2H_4$ | vol % $C_3H_6$ | vol % $C_4H_8$ |
|---|---|---|---|---|
| °C. | °F. | Conversion | Conversion | Conversion |
| 100 | 221 | 41.5 | 11.7 | 8.6 |
| 120 | 248 | 82.4 | 38.4 | 23.5 |
| 140 | 284 | 97.6 | 70.4 | 50.1 |
| 160 | 320 | 99.9 | 87.9 | 71.7 |
| 180 | 356 | 100.0 | 99.1 | 97.0 |
| 200 | 392 | 100.0 | 100.0 | 100.0 |
| 220 | 428 | 100.0 | 100.0 | 100.0 |
| 240 | 464 | 100.0 | 100.0 | 100.0 |
| 260 | 500 | 100.0 | 100.0 | 100.0 |
| 280 | 536 | 100.0 | 100.0 | 100.0 |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

The indefinite articles "a" and "an" as used herein mean one or more when applied to any feature in embodiments of the present invention described in the specification and claims. The use of "a" and "an" does not limit the meaning to a single feature unless such a limit is specifically stated. The definite article "the" preceding singular or plural nouns or noun phrases denotes a particular specified feature or particular features and may have a singular or plural connotation depending upon the context in which it is used. The adjective "any" means one, some or all indiscriminately of whatever quantity.

What is claimed is:

1. A process for hydrogenating olefins, said process comprising:
    introducing a feed gas comprising an olefin having one point of unsaturation at a concentration greater than 6 mole %, H2, and at least one sulfur compound through an inlet of a reactor vessel at an inlet temperature from 100° C. to 250° C., said reactor vessel containing a bed of a sulfided metal catalyst said catalyst comprising from 2 wt % to 20 wt % NiO and from 9wt % to 40 wt % $MoO_3$ on an unsulfided basis supported on an alumina support;
    contacting said olefin having one point of unsaturation and said $H_2$ with said catalyst to react said olefin having one point of unsaturation and said $H_2$ under reaction conditions effective to hydrogenate said olefin having one point of unsaturation to produce a saturated hydrocarbon; and
    withdrawing an outlet gas mixture comprising said saturated hydrocarbon from said reactor vessel through an outlet at an outlet temperature from 120° C. to 425° C., wherein said reactor is operated adiabatically.

2. The process according to claim 1, wherein said feed gas comprises an organic sulfur compound and said process further comprising contacting said organic sulfur compound and said $H_2$ with said catalyst at a temperature from 120° C. to 425° C. thereby forming $H_2S$ from said organic sulfur compound.

3. The process according to claim 2, wherein said organic sulfur compound is selected from the group consisting of carbonyl sulfide, carbon disulfide, mercaptans, dialkyl sulfides, dialkyl disulfides, thiophenic species, and combinations thereof 4. The process according to claim 2, wherein said outlet gas mixture comprises said $H_2S$.

5. The process according to claim 1 or claim 2, further comprising:
    introducing said outlet gas mixture into a second reactor containing a chemical adsorbent comprising ZnO;
    contacting said outlet gas mixture with said chemical adsorbent at a temperature from 200° C. to 425° C. to remove sulfur therefrom thereby forming a sulfur depleted outlet gas mixture; and
    withdrawing said sulfur depleted outlet gas mixture from said second reactor.

6. The process according to claim 1, wherein said inlet temperature is from 100° C. to 175° C.

7. The process according to claim 1, wherein said inlet temperature is from 100° C. to 225° C.

8. The process according to claim 1, wherein said outlet temperature is from 300° C. to 425° C.

9. The process according to claim 1, wherein said catalyst comprises 3 to 4 wt % NiO on an unsulfided basis.

10. The process according to claim 1, wherein said catalyst comprises 9 to 11 wt % $MoO_3$ on an unsulfided basis.

11. The process according to claim 1, wherein said catalyst comprises 5 to 6 wt% NiO on an unsulfided basis.

12. The process according to claim 1, wherein said catalyst comprises 24 to 26 wt % $MoO_3$ on an unsulfided basis.

13. The process according to claim 1, wherein said feed gas is introduced through the inlet of the reactor vessel with a flow rate that provides a gas hourly space velocity from 400 to 6000 $hr^{-1}$.

14. The process according to claim 1, wherein the olefin concentration is up to 14 mole % olefins.

15. The process according to claim 1, wherein the olefin concentration is up to 30 mole % olefins.

16. The process according to claim 1, wherein said feed gas comprises an amount $H_2$ to prevent hydrocarbon cracking.

17. The process according to claim 1, wherein said feed gas comprises an amount $H_2$ to maintain at least 2 mole % $H_2$ in said outlet gas mixture.

18. The process according to claim 1, wherein said feed gas and said $H_2$ are contacted with said catalyst at a pressure from 0.6 MPa to 5 MPa.

19. The process according to claim 1, wherein said feed gas comprises an organic sulfur compound and said process further comprising contacting said organic sulfur compound and said $H_2$ downstream with a different catalyst selected from the group consisting of cobalt-molybdenum, nickel molybdenum, cobalt-tungsten, nickel tungsten, nickel-cobalt-molybdenum based catalysts and combinations thereof at a temperature from 200° C. to 425° C. thereby forming $H_2S$ from said at least one organic sulfur compound.

20. A process for hydrogenating olefins having one point of unsaturation at a concentration greater than 6 mole %, in a feed gas also comprising H2 and at least one sulfur compound, said process comprising adiabatically reacting said olefins having one point of unsaturation with said H2 in the presence of a bed of a sulfided catalyst comprising from 2 wt % to 20 wt % NiO and 9 wt % to 40 wt % MoO3 on an unsulfided basis, supported on an alumina support, at an initial temperature from 100° C. to 250° C. to hydrogenate said olefins having one point of unsaturation to produce an outlet gas mixture comprising saturated hydrocarbons.

21. The process according to claim 20, further comprising removing said outlet gas mixture from the presence of said catalyst at a temperature from 120° C. to 425° C.

22. The process according to claim 21, wherein said at least one sulfur compound comprises at least one organic sulfur compound, and said process further comprises further contacting said outlet gas mixture with said catalyst at a temperature from 120° C. to 425° C. thereby forming $H_2S$ from said at least one organic sulfur compound.

23. The process according to claim 22, wherein said process further comprises contacting said outlet gas mixture with a second catalyst selected from the group consisting of a different Ni/Mo catalyst and a Co/Mo catalyst at a temperature from 200° C. to 425° C. thereby forming $H_2S$ from said at least one organic sulfur compound.

24. A process for preparing a feed gas for steam methane reforming from a feed gas comprising at least one olefin having one point of unsaturation at a concentration greater than 6 mole %, $H_2$ and at least one organic sulfur compound, said process comprising:

adiabatically reacting said olefin having one point of unsaturation with said $H_2$ in the presence of a bed of a sulfided catalyst comprising from 2 wt % to 20 wt % NiO and 9 wt% to 40 wt % $MoO_3$ on an unsulfided basis supported on an alumina support, at an initial temperature from 100° C. to 250° C. to hydrogenate said olefin having one point of unsaturation, thereby producing an outlet gas mixture comprising saturated hydrocarbons;

further contacting said saturated hydrocarbon-containing outlet gas mixture with said catalyst at a temperature from 120° C. to 425° C. thereby forming $H_2S$ from said at least one organic sulfur compound;

removing said outlet gas mixture from the presence of said catalyst at a temperature from 120° C. to 425° C.; and contacting said $H_2S$-containing outlet gas mixture with a chemical adsorbent comprising ZnO at a temperature from 200° C. to 425° C. to remove sulfur therefrom.

25. The process according to claim 1, wherein the alumina support accounts for the balance of the weight of the catalyst.

26. The process according to claim 24, wherein the alumina support accounts for the balance of the weight of the catalyst.

27. The process according to claim 1, wherein the olefin of the feed gas comprises one or more of ethylene, propylene, or butene.

* * * * *

UNITED STATES PATENT AND TRADEMARK OFFICE
CERTIFICATE OF CORRECTION

| | | |
|---|---|---|
| PATENT NO. | : 8,664,459 B2 | Page 1 of 1 |
| APPLICATION NO. | : 12/264443 | |
| DATED | : March 4, 2014 | |
| INVENTOR(S) | : Davis et al. | |

It is certified that error appears in the above-identified patent and that said Letters Patent is hereby corrected as shown below:

On the Title Page, item (56) Column 2, within "References Cited" beneath "U.S. PATENT DOCUMENTS" "Farha et al." should read "Farha, Jr. et al."

In the Claims:

Claim 1, Column 10, Line 6, "mole %, H2," should read "mole %, $H_2$,"

Claim 1, Column 10, Line 9, "of a sulfided metal catalyst said" should read "of a sulfided metal catalyst, said"

Claim 3, Column 10, Line 33, "tions thereof" should read "tions thereof."

Claim 20, Column 11, Line 20, "feed gas also comprising H2" should read "feed gas also comprising $H_2$"

Claim 20, Column 11, Line 22, "unsaturation with said H2" should read "unsaturation with said $H_2$"

Claim 20, Column 11, Line 24, "to 40 wt % MoO3" should read "to 40 wt % $MoO_3$"

Signed and Sealed this
Twenty-ninth Day of September, 2015

Michelle K. Lee
*Director of the United States Patent and Trademark Office*